(12) United States Patent
Amit et al.

(10) Patent No.: US 10,828,000 B2
(45) Date of Patent: Nov. 10, 2020

(54) MEDICAL IMAGE DATA ANALYSIS

(71) Applicant: International Business Machines Corporation, Armonk, NY (US)

(72) Inventors: Guy Amit, Ganei Tikva (IL); Rami Ben-Ari, Tel-Aviv (IL); Tal Tlusty Shapiro, Zichron Yaacov (IL)

(73) Assignee: International Business Machines Corporation, Armonk, NY (US)

( * ) Notice: Subject to any disclaimer, the term of this patent is extended or adjusted under 35 U.S.C. 154(b) by 84 days.

(21) Appl. No.: 16/199,187

(22) Filed: Nov. 25, 2018

(65) Prior Publication Data
US 2020/0163641 A1    May 28, 2020

(51) Int. Cl.
*G06K 9/00* (2006.01)
*A61B 6/00* (2006.01)
(Continued)

(52) U.S. Cl.
CPC .............. *A61B 6/5217* (2013.01); *A61B 6/12* (2013.01); *A61B 6/502* (2013.01); *G06K 9/6219* (2013.01);
(Continued)

(58) Field of Classification Search
CPC ......... A61B 5/033; A61B 5/015; A61B 5/055; A61B 5/4312; A61B 5/441; A61B 5/7267; A61B 6/5217; A61B 6/12; A61B 6/502; A61B 2090/374; A61B 2090/3762; A61B 2090/378; A61B 34/10; G06K 9/6233; G06K 9/6272; G06K 9/6219; G06K 9/6227; G06K 9/6232; G06K 9/6256; G06K 9/6262; G06K 9/6269; G06K 9/627; G06K 9/6265; G06K 9/66; G06K 9/62; G06K 9/621; G06K 9/6218; G06K 9/6221; G06K 9/6224; G06K 9/6226; G06K 9/4642; G06K 9/4647; G06K 9/4652; G06K 9/4661; G06K 9/4604; G06K 9/00288; G06K 9/3233;
(Continued)

(56) References Cited

U.S. PATENT DOCUMENTS 5,970,164 A * 10/1999 Bamberger ............... G06T 5/40
378/37
7,903,861 B2    3/2011 Luo et al.
(Continued)

OTHER PUBLICATIONS

Lee, Juhun et al., Automated mammographic breast density estimation using a fully convolutional network, Medical Physics, published Jan. 24, 2018, https://doi.org/10.1002/mp.12763, 3 pp.
(Continued)

*Primary Examiner* — Jose L Couso
(74) *Attorney, Agent, or Firm* — Barry D. Blount (57) ABSTRACT

A system for analyzing image data can include a processor to detect a set of medical images and partition each medical image into a plurality of non-overlapping or overlapping patches. The processor can also generate an ordered set of patch clusters derived from the medical images, wherein the patch clusters are sorted based on a type of tissue identified in each of the medical images. Additionally, the processor can generate a digital representation of a percentage of the type of tissue calculated for each of the medical images and transmit an alert in response to detecting that the percentage of the type of tissue for an image exceeds a predetermined threshold.

20 Claims, 9 Drawing Sheets

(51) Int. Cl.
*G16H 30/20* (2018.01)
*G06N 20/10* (2019.01)
*G06T 7/00* (2017.01)
*G06K 9/62* (2006.01)
*A61B 6/12* (2006.01)

(52) U.S. Cl.
CPC ......... *G06K 9/6223* (2013.01); *G06K 9/6272* (2013.01); *G06N 20/10* (2019.01); *G06T 7/0012* (2013.01); *G16H 30/20* (2018.01); *G06T 2207/20021* (2013.01); *G06T 2207/20081* (2013.01); *G06T 2207/20084* (2013.01); *G06T 2207/30068* (2013.01)

(58) Field of Classification Search
CPC . G06T 2207/20021; G06T 2207/20081; G06T 2207/20084; G06T 2207/30068; G06T 2207/10088; G06T 2207/30004; G06T 2207/30088; G06T 2207/10081; G06T 2207/10104; G06T 2207/10116; G06T 2207/10108; G06T 2207/10132; G06T 2207/20076; G06T 7/0012; G06T 7/0014; G06T 7/44; G06T 7/73; G06T 7/74; G06T 7/0016; G06T 7/136; G06T 7/11; G06T 7/143; G06T 7/162; G06T 7/337; G06T 7/62; G06T 2200/24; G06T 2210/41; G16H 30/20; G16H 15/00; G16H 50/00; G16H 50/50; G16H 50/20; G16H 10/60; G06N 20/10; G06N 20/00; G06N 3/08; G06N 3/084; G06N 3/088; G06N 3/02; G06N 3/0454; G06N 7/005; G06Q 50/24; G06F 19/00; G06F 19/321; G06F 19/3418; G06F 19/36; H04N 5/2351; H04N 5/332
See application file for complete search history.

(56) References Cited

U.S. PATENT DOCUMENTS

| | | | |
|---|---|---|---|
| 9,519,966 B2 | 12/2016 | Ghouti et al. | |
| 9,704,059 B2 | 7/2017 | Alpert et al. | |
| 9,895,121 B2 | 2/2018 | Abdolell et al. | |
| 2004/0184644 A1* | 9/2004 | Leichter | G06K 9/033 382/128 |
| 2006/0171573 A1* | 8/2006 | Rogers | G06K 9/3233 382/128 |
| 2007/0206844 A1* | 9/2007 | Russakoff | G06K 9/38 382/132 |
| 2010/0124364 A1* | 5/2010 | Huo | G06T 7/0012 382/128 |
| 2010/0128063 A1* | 5/2010 | Huo | G06F 19/321 345/620 |
| 2011/0206261 A1* | 8/2011 | Huo | G06F 19/321 382/132 |
| 2015/0070385 A1* | 3/2015 | Ishizu | A61B 8/0825 345/632 |
| 2017/0249739 A1 | 8/2017 | Kallenberg et al. | |
| 2020/0020098 A1* | 1/2020 | Odry | G06N 3/0454 |

OTHER PUBLICATIONS

Mohamed, Aly A., et al., A deep learning method for classifying mammographic breast density categories, Med. Phys. 45(1), Jan. 2018, 0094-2405/2018/45(1)/314/8, pp. 8.

Rajkumar, K. K., Chapter 7, Unsupervised Learning Techniques for Mammogram Classification, SHODHGANGA: a reservoir of Indian theses@inflibnet, Upload Date: Nov. 20, 2014, pp. 19.

Tlusty, Tal, et al., Unsupervised clustering of mammograms for outlier detection and breast density estimation, International Conference on Pattern Recognition, 2018, pp. 4.

* cited by examiner

MEDICAL IMAGE DATA ANALYSIS

BACKGROUND

The present disclosure relates to analyzing image data, and more specifically, but not exclusively, to analyzing medical images to detect abnormalities.

SUMMARY

According to an embodiment described herein, a system for analyzing image data can include a processor to detect a set of medical images and partition each medical image into a plurality of non-overlapping patches. The processor can also generate a sorted set of patch clusters derived from the medical images, wherein the patch clusters are sorted based on a type of tissue identified in each of the medical images. Additionally, the processor can generate a digital representation of a percentage of the type of tissue calculated for each of the medical images and transmit an alert in response to detecting that the percentage of the type of tissue for at least one image exceeds a predetermined threshold.

In some embodiments, a system for analyzing medical images can include a processor to train an auto-encoder to detect a latent space feature within a set of medical images. The processor can also generate a set of clusters based on encoding of the medical images with the latent space features and generate an encoding of the medical images based on distances between the medical images and the cluster centers. Additionally, the processor can generate a hierarchical clustering representation of the encoded medical images, and detect at least one outlier in the medical images based on the hierarchical clustering representation. Furthermore, the processor can generate an alert indicating that a revised set of medical image data is generated, the revised set of medical image data to exclude the at least one outlier.

In yet another embodiment, a computer program product for analyzing image data can include a computer readable storage medium having program instructions embodied therewith, wherein the computer readable storage medium is not a transitory signal per se. The program instructions can be executable by a processor to cause the processor to detect a set of medical images and partition each medical image into a plurality of non-overlapping patches. The program instructions can also cause the processor to generate a sorted set of patch clusters derived from the medical images, wherein the patch clusters are sorted based on a type of tissue identified in each of the medical images. Additionally, the program instructions can also cause the processor to generate a digital representation of a percentage of the type of tissue calculated for each of the medical images and transmit an alert in response to detecting that the percentage of the type of tissue for at least one image exceeds a predetermined threshold.

DETAILED DESCRIPTION

The increased use of machine learning for cognitive tasks has driven an increased demand for large annotated training datasets. In the medical imaging domain, such datasets are scarce, and the process of labeling them is costly, error prone and requires high expertise. Unsupervised learning is therefore an attractive approach for analyzing unlabeled medical images. Techniques herein include an unsupervised analysis method consisting of feature learning by stacked auto-encoders (SAEs) for building a data model, and encoding of new images using the data model. The techniques can be applied to medical images for image-level and patch-level analysis of breast mammograms. At the image-level, techniques herein use cluster-based image encoding to identify outlier images such as images with implants or non-standard acquisition views. At the patch-level, image signatures using patch clustering can be used for unsupervised semantic segmentation of breast tissues, as well as for separating mammograms with high and low breast density. Accordingly, in embodiments described herein, using unsupervised analysis of unannotated data can provide insights about the dataset, filter relevant images, suggest unbiased image classification, and guide the annotation process. Furthermore, unsupervised methods can be applied to process sub-image entities, such as patches, to facilitate semantic segmentation and automated abnormality detection tasks.

One example of medical image data that can be analyzed with unsupervised deep learning techniques described herein includes digital mammography, which is used to screen and diagnose breast cancer. With the large volumes of mammography examinations, vast image datasets often exist at clinical institutions. However, their use by machine learning algorithms is limited due the lack of annotation or labeling. The heterogeneity of data, which may contain special images that represent uncommon conditions, sets a further obstacle since certain types of images are to be excluded from the learning process. Unsupervised deep learning methods can learn efficient image representation in lower-dimension feature space. Following dimensionality reduction, the images can be clustered and their interrelations can be visualized. In some embodiments, a feature representation is detected and a clustering is applied in a subspace. Auto-Encoders (AE) can be used to implement deep learning techniques described herein. In one example, an unsupervised clustering can analyze medical images such as mammograms. In some embodiments, stacked auto-encoders can extract image features and apply clustering analysis to assign semantic labels to the data. Techniques herein include a detection of outlier images with distinct global characteristics in a large dataset. The outlier images can include breast implants or a non-standard imaging view. Techniques also include patch-based semantic segmentation of the breast to estimate breast density and determine a probability of an abnormality of medical condition in a medical image.

Figure 1:
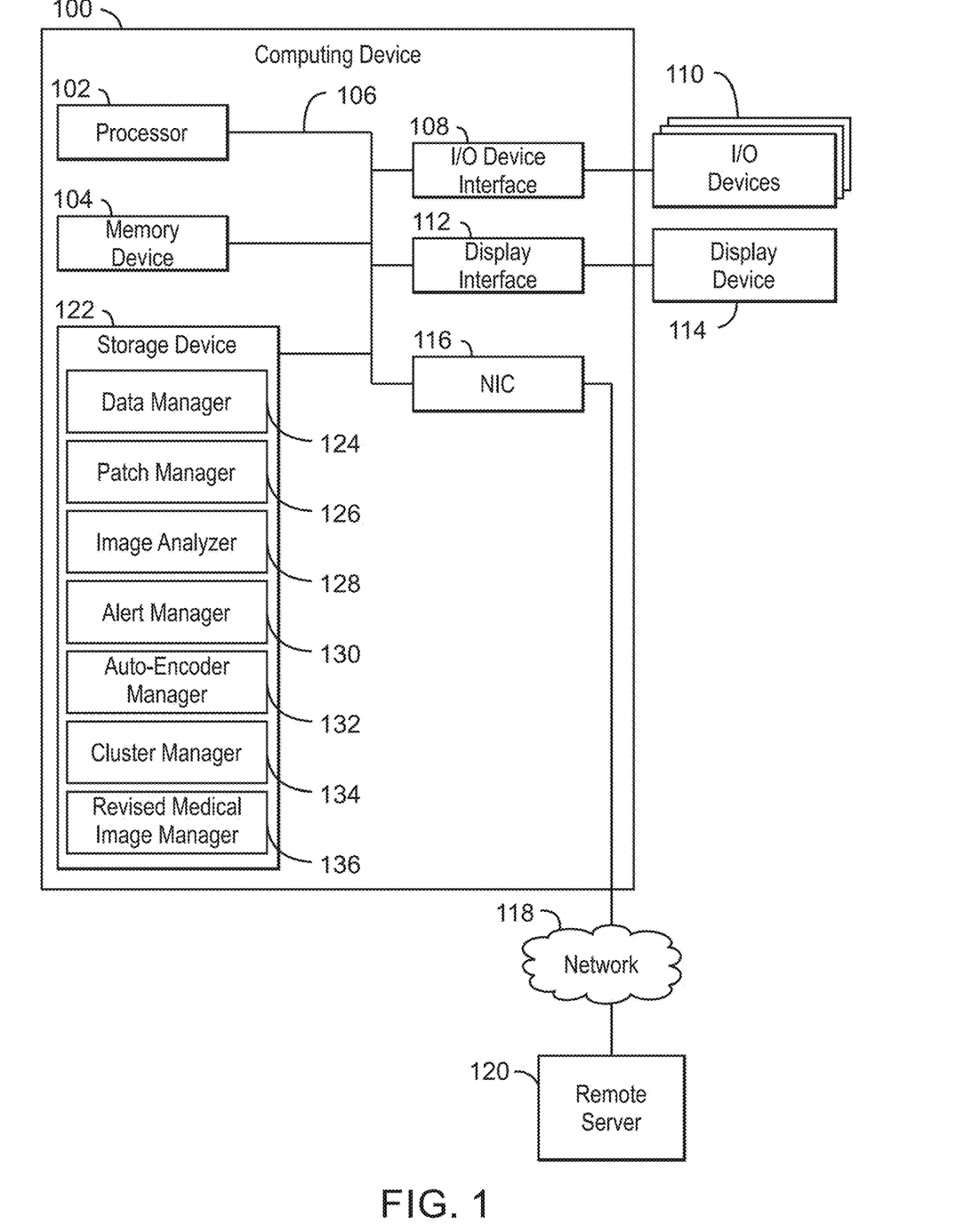
FIG. 1 depicts a block diagram of an example computing system that can analyze medical images according to an embodiment described herein.

With reference now to FIG. 1, an example computing device is depicted that can analyze medical images. The computing device 100 may be for example, a server, desktop computer, laptop computer, tablet computer, or smartphone. In some examples, computing device 100 may be a cloud computing node. Computing device 100 may be described in the general context of computer system executable instructions, such as program modules, being executed by a computer system. Generally, program modules may include routines, programs, objects, components, logic, data structures, and so on that perform particular tasks or implement particular abstract data types. Computing device 100 may be practiced in distributed cloud computing environments where tasks are performed by remote processing devices that are linked through a communications network. In a distributed cloud computing environment, program modules may be located in both local and remote computer system storage media including memory storage devices.

The computing device 100 may include a processor 102 that is adapted to execute stored instructions, a memory device 104 to provide temporary memory space for operations of said instructions during operation. The processor can be a single-core processor, multi-core processor, computing cluster, or any number of other configurations. The memory 104 can include random access memory (RAM), read only memory, flash memory, or any other suitable memory systems.

The processor 102 may be connected through a system interconnect 106 (e.g., PCI®, PCI-Express®, etc.) to an input/output (I/O) device interface 108 adapted to connect the computing device 100 to one or more I/O devices 110. The I/O devices 110 may include, for example, a keyboard and a pointing device, wherein the pointing device may include a touchpad or a touchscreen, among others. The I/O devices 110 may be built-in components of the computing device 100, or may be devices that are externally connected to the computing device 100.

The processor 102 may also be linked through the system interconnect 106 to a display interface 112 adapted to connect the computing device 100 to a display device 114. The display device 114 may include a display screen that is a built-in component of the computing device 100. The display device 114 may also include a computer monitor, television, or projector, among others, that is externally connected to the computing device 100. In addition, a network interface controller (NIC) 116 may be adapted to connect the computing device 100 through the system interconnect 106 to the network 118. In some embodiments, the NIC 116 can transmit data using any suitable interface or protocol, such as the internet small computer system interface, among others. The network 118 may be a cellular network, a radio network, a wide area network (WAN), a local area network (LAN), or the Internet, among others. A remote server 120 may connect to the computing device 100 through the network 118.

The processor 102 may also be linked through the system interconnect 106 to a storage device 122 that can include a hard drive, an optical drive, a USB flash drive, an array of drives, or any combinations thereof. In some examples, the storage device 122 may include data and applications used to execute instructions by the processor 102. In some examples, the storage device 122 can include a data manager 124, a patch manager 126, an image analyzer 128, and an alert manager 130. In some embodiments, the data manager 124 can detect a set of medical images. The patch manager 126 can partition each medical image into a plurality of non-overlapping patches. In some examples, the patch manager 126 can also generate a sorted set of patch clusters derived from the medical images, wherein the patch clusters are sorted based on a type of tissue identified in each of the medical images. In some embodiments, an image analyzer 128 can generate a digital representation of a percentage of the type of tissue calculated for each of the medical images. In some embodiments, an alert manager 130 can transmit an alert in response to detecting that the percentage of the type of tissue for an image exceeds a predetermined threshold.

In some examples, the storage device 122 can also include an auto-encoder manager 132 that can train an auto-encoder to detect latent space features within a set of medical images. Additionally, the storage device 122 can include a cluster manager 134 that can generate a set of clusters based on encoding of the medical images with the latent space features. The cluster manager 134 can also generate an encoding of the medical images based on distances between the medical images and the cluster centers. Additionally, the cluster manager 134 can generate a hierarchical clustering representation of the encoded medical images. Furthermore, the cluster manager 134 can detect at least one outlier in the medical images based on the hierarchical clustering representation. Furthermore, the storage device 122 can include a revised medical image manager 136 that can generate an alert indicating that a revised set of medical image data is generated. In some examples, the revised set of medical image data exclude the at least one outlier.

It is to be understood that the block diagram of FIG. 1 is not intended to indicate that the computing device 100 is to include all of the components shown in FIG. 1. Rather, the computing device 100 can include fewer or additional components not illustrated in FIG. 1 (e.g., additional memory components, embedded controllers, modules, additional network interfaces, etc.). Furthermore, any of the functionalities of the data manager 124, patch manager 126, image analyzer 128, alert manager 130, auto-encoder manager 132, cluster manager 134, and revised medical image manager 136 are partially, or entirely, implemented in hardware and/or in the processor 102. For example, the functionality may be implemented with an application specific integrated circuit, logic implemented in an embedded controller, or in logic implemented in the processor 102, among others. In some embodiments, the functionalities of the data manager 124, patch manager 126, image analyzer 128, alert manager 130, auto-encoder manager 132, cluster manager 134, and revised medical image manager 136 can be implemented with logic, wherein the logic, as referred to herein, can include any suitable hardware (e.g., a processor, among others), software (e.g., an application, among others), firmware, or any suitable combination of hardware, software, and firmware.

Figure 2:
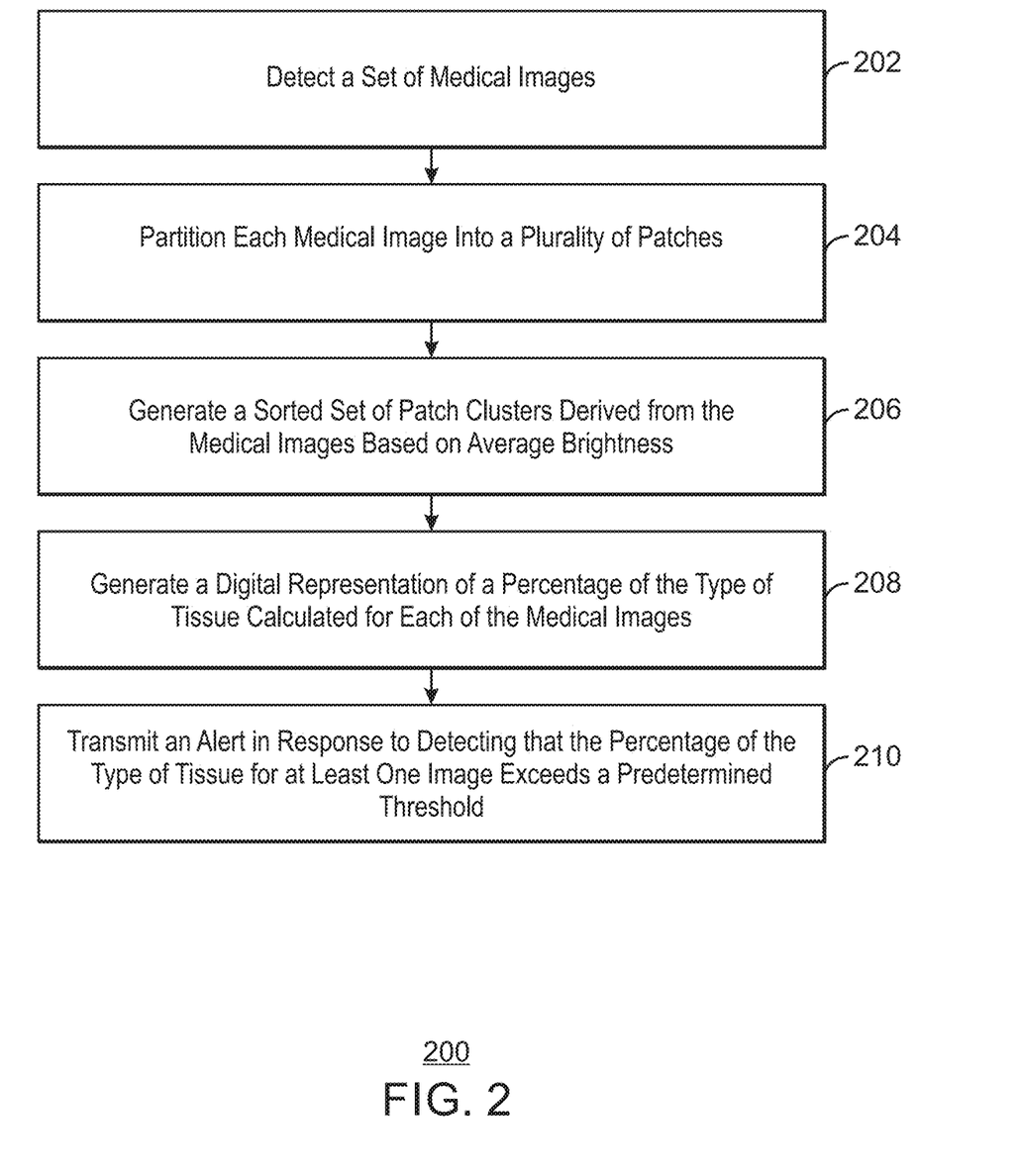
FIG. 2 is a process flow diagram of an example method that can generate an alert for medical images according to an embodiment described herein.

FIG. 2 is a process flow diagram of an example method that can generate an alert based on analysis of medical images. The method 200 can be implemented with any suitable computing device, such as the computing device 100 of FIG. 1.

At block 202, the data manager 124 can detect a set of medical images. In some embodiments, the medical images can include x-ray images of breast tissue from mammograms, or any other suitable medical image. In some examples, the set of medical images can include any number of different medical images from any number of patients.

For example, the set of medical images can include mammograms from different perspectives or angles, among others.

At block 204, the patch manager 126 can partition each medical image into a plurality of overlapping or non-overlapping patches. In some embodiments, the patches are a fixed size and can be extracted from the interior area of the medical image using a sliding window with an overlap. In some examples, the overlap can be any suitable percentage value such as ten percent, twenty percent, fifty percent, and the like. In some embodiments, the size of the patches can be modified or can vary.

At block 206, the patch manager 126 can generate a sorted set of patch clusters derived from the medical images, wherein the patch clusters are sorted based on an average brightness of each patch. The average brightness can indicate a type of tissue identified in each of the medical images. In some embodiments, the patch manager 126 can generate the patches with an unsupervised machine learning technique or analysis pipeline based on sub-image patches in attempt to capture local image characteristics. The patches can be extracted from the interior area of the medical image using a sliding window with any suitable overlap. The patches from the images can be used for training the stacked auto-encoders (SAE) to learn a compact feature representation in an unsupervised manner In some embodiments, these features can encode patch textures. For example, the patch textures can indicate fatty tissue or dense tissue in a mammogram. Each image Xi is represented by the collection of the image's corresponding patches $X_i = \cup_j x_{ij}$, wherein i and j indicate the image and the patch index respectively. The SAE can map each patch to a lower dimensional space $H_{\theta,e}: x \to \tilde{f}$, wherein $f \in \mathbb{R}^D$ is the feature vector of the patch in the auto-encoder latent space. The image patches can then be clustered by K-means to $c_p$ clusters. Consequently, the content of each medical image or mammogram can be represented by the patch clusters ID as visualized in FIG. 4.

At block 208, the image analyzer 128 can generate a digital representation of an image according to the prevalence of patches from different clusters. In some examples, the prevalence of patches from different clusters indicate different types of tissues. The image analyzer 128 can also generate the digital representation of the image based on a percentage of a type of tissue calculated for each of the medical images. In some examples, the percentage of the type of tissue corresponds to a breast density. For example, patches of a first cluster can consistently correspond to fat tissues, while high intensity patches can be associated with fibroglandular (FG) tissues. The patch distribution within the image can be used for semantic segmentation of the breast tissue, separating between FG and fat regions. Since areas with FG tissues appear as bright patterns, the patch manager 126 can sort the clusters by the mean intensity of all patches associated with that cluster, $S: C_k \to C_K^S$. The FG segmentation can then be derived by setting a cut-off cluster such as $c_f = \lceil c_p/2 \rceil$, wherein patches belonging to clusters in $C_K^S$ with $k \geq c_f$ are identified as FG tissue.

For breast density or type of tissue category classification, the patch manager 126 can create an image signature, $g^i \in \mathbb{R}^{c_p}$ by a normalized histogram of the patches in the mammogram image associated with each cluster. The percentage of FG tissue within the breast, also known as Percentage of Mammographic Density (PMD) can be computed as a normalized sum of patches that are labeled as FG, i.e. $PMD = \Sigma_{k \geq c_f}^{C_p} g_k^i$. The cutoff $c_f$ is equivalent to an intensity threshold but in a rich patch texture space. In some examples, certain patch clusters are more common in dense breasts and thus can specifically be used for breast density classification. Alternatively, one can classify the breast density in an unsupervised manner by applying K-means in the image signature space or subspace. In some embodiments, the image analyzer 128 can calculate the breast density according to the prevalence of patches from certain clusters. Additionally, the image analyzer 128 can detect a likelihood of a medical condition in response to the detected mean intensity of a patch cluster being above a threshold. For example, the image analyzer 128 can detect a likelihood of breast cancer when a breast has a high density.

At block 210, the alert manager 130 can transmit an alert in response to detecting that the percentage of the type of tissue for an image exceeds a predetermined threshold. In some embodiments, the alert manager 130 transmits an alert for each image that has a percentage of a type of tissue that exceeds the predetermined threshold. For example, the alert manager 130 can transmit the alert to a remote device or to a user associated with a predetermined access level. In some embodiments, the alert manager 130 can modify the operation of a medical device, such as an x-ray machine. For example, the alert manager 130 can prevent subsequent operation of a medical device for a predetermined period of time in response to detecting an alert. The alert manager 130 can display a warning that the percentage of the type of tissue for an image exceeds a predetermined threshold. In some embodiments, the alert manager 130 can automatically schedule and/or conduct additional operations to further analyze the image to determine if a mammogram is associated with breast cancer or any other suitable medical condition.

The process flow diagram of FIG. 2 is not intended to indicate that the operations of the method 200 are to be executed in any particular order, or that all of the operations of the method 200 are to be included in every case. Additionally, the method 200 can include additional operations. In some embodiments, the method 200 can include calculating the type of tissue for each patch cluster within the medical images based on an unsupervised machine learning technique. In some examples, the method 200 can include dividing each medical image into a predetermined number of overlapping bounding boxes that correspond to the patch clusters.

Figure 3:
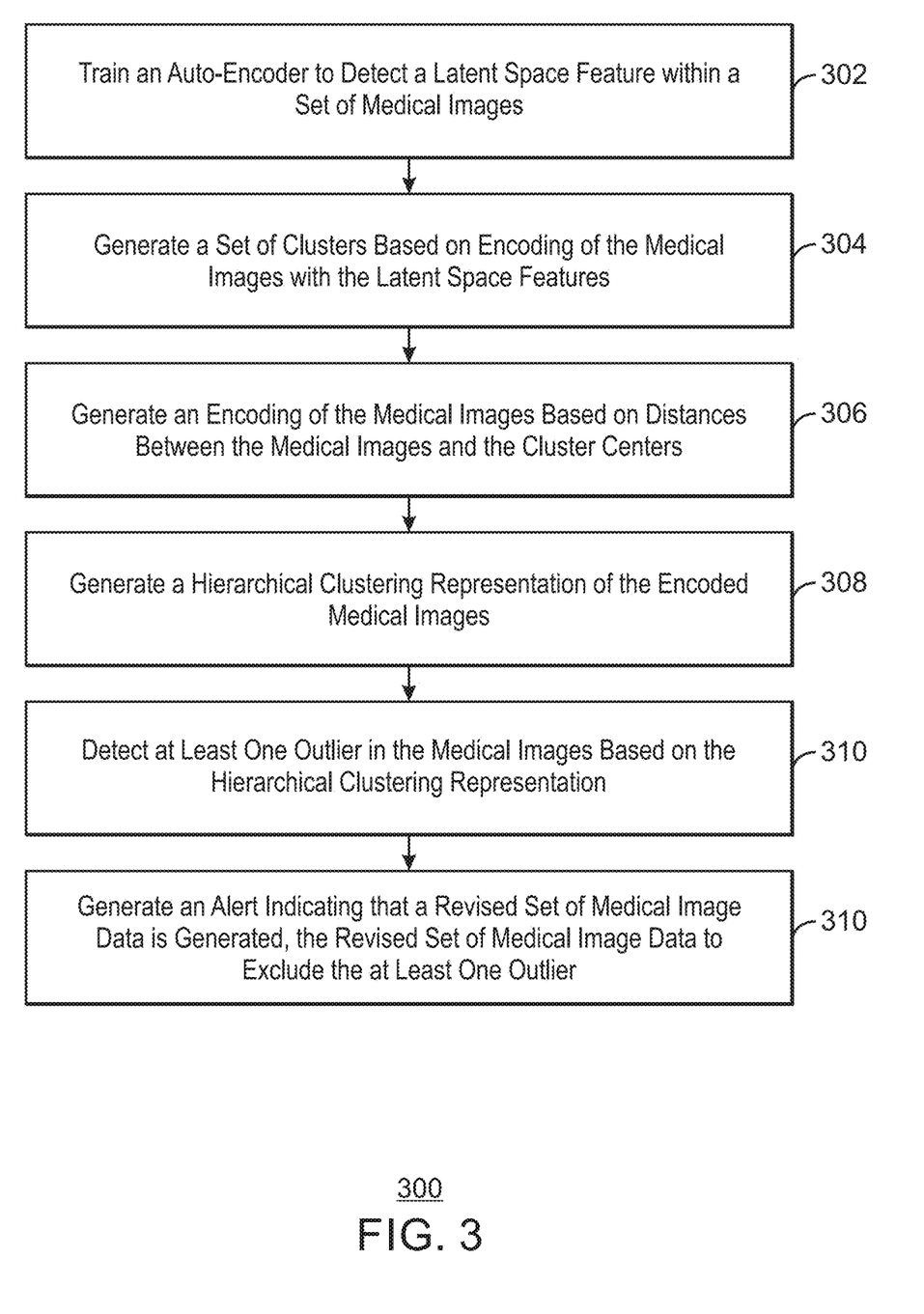
FIG. 3 is a process flow diagram of an example method that can train an auto-encoder to generate an alert for medical images according to an embodiment described herein.

FIG. 3 is a process flow diagram of an example method that can train an auto-encoder to generate an alert for medical images. The method 300 can be implemented with any suitable computing device, such as the computing device 100 of FIG. 1.

At block 302, an auto-encoder manager 132 can train an auto-encoder to generate a short representation of an image or latent space feature within a set of medical images. In some embodiments, the auto-encoder manager 132 can include a deep auto-encoder for the feature-space representation of whole images and sub-image patches extracted from a medical image such as a mammogram. The auto-encoder can create patch clusters, wherein the auto-encoder is a fully-connected neural network configured to calculate a feature vector representing each patch. For encoding, the auto-encoder manager 132 can use a nonlinear function $H_{\theta,e}: X \to F$ to map the input data $X_i \in X$, which can be the whole mammogram or an image patch, from the data space X to a new low dimension feature space $F \in \mathbb{R}^D$. In some examples, D is the feature space dimension and $\theta$, e are the learned parameters. Likewise, the nonlinear mapping $H_{\theta,d}$ describes the decoder function that maps the features back to the input space. Specifically, the auto-encoder manager 132 can use a denoising SAE formulation, which can be formulated as follows:

$$I' \approx \text{Dropout}\{I\} \quad (1)$$

$$H_{\theta,e} = H_e(W_e I' + b_e) \quad (2)$$

$$\tilde{H}\theta, e \approx \text{Dropout}\{H_{\theta,e}\} \quad (3)$$

$$\tilde{I} = H_d(W_d \tilde{H}\theta, e + b_d) \quad (4)$$

In Eq(1), I is a subset of n points $\{X_i \in X\}_{i=1}^n$, wherein $H_e$ and $H_d$ are the encoder activation function and the decoder activation function, respectively. In some examples, $\theta$, $e = \{W_e, b_e\}$ and $\theta$, $d = \{W_d, b_d\}$, which are the model's learned parameters. The SAE is composed of multiple layers of denoising auto-encoders that are stacked such that the output of each layer is randomly corrupted by a dropout layer, which sets some of the dropout layer's inputs to zero. The corrupted output is then fed as the input to the next layer. In some embodiments, rectified linear units (ReLUs) are applied to all encoder/decoder pairs except the first and the last. In the training process of the SAE, the loss function is defined as the reconstruction $\|I - \tilde{I}\|_2^2$. Each layer is trained separately while other layers are kept frozen. Each layer is initialized by the previous layer output. The training is finalized after end-to-end fine tuning. For feature extraction, the output from the lowest dimension layer is detected.

At block 304, a cluster manager 134 can generate a set of clusters based on encoding of the medical images with the latent space features. In some embodiments, the cluster manager 134 can use a training set to build a cluster-based representation of the expected images, such as craniocaudal views and mediolateral oblique views, in the feature space. Then, the cluster manager 134 can use this representation to encode new images and evaluate the correspondence between the unsupervised clusters and the global labels of the images. In some embodiments, the ground-truth labels can be used for validation and the auto-encoder can be trained using the training set.

At block 306, the cluster manager 134 can generate an encoding of the medical images based on distances between the medical images and the cluster centers. For example, the encoded training images, such as a feature vectors of sixty-four dimensions, among others, can be clustered using K-means to produce cluster centers $\{C_1, \ldots, C_{ci}\}$. These clusters contain images with similar global characteristics. The cluster manager 134 can use the cluster centers to encode a new test image $X_i$ based on Equation 6 below.

$$d^i = (d_1^i, \ldots, d_{c_i}^i) := D(f^i, C_k) \quad (5)$$

In this equation, D is a distance function and $f^i$ is the representation of the image in the auto-encoder latent space F. This type of image encoding is designed to differentiate between the outlier and the standard images, based on their distances from the cluster centers. For final class assessment, the cluster manager 134 can cluster the test images, according to $d^i$, into k sub-groups. Correspondence between the clusters and the ground-truth labels of the test images can be assessed by calculating the cluster purity defined by Equation 7 below.

$$\text{purity}(\Omega, L) = \sum_{k=1}^{m} \max_j |w_k \cap l_j| \quad \text{Eq (6)}$$

In some examples, $\Omega = w_1, \ldots, w_m$ is the set of clusters and $L = l_1, \ldots, l_m$ is the set of class labels. The cluster purity is an unsupervised measure for classification accuracy, wherein a cluster's label is determined by the majority label of its images, and an image is correctly classified if the image has the same label as the cluster. Otherwise, the image is considered misclassified. This enables the cluster manager 134 to calculate the sensitivity and specificity of the classification. The cluster manager 134 can also evaluate min(di), the distance to the nearest cluster center, to discriminate between image classes. In some embodiments, this is measured by the area under the receiver operator characteristics curve (AUC).

At block 308, the cluster manager 134 can generate a hierarchical clustering representation of the encoded medical images. The hierarchical clustering representation can indicate if a cluster corresponds to a control image or an anomaly such as a breast implant in mammogram images. In some embodiments, the hierarchical clustering representation indicates if a cluster corresponds to a false positive or a false negative associated with a medical condition.

At block 310, the cluster manager 134 can detect at least one outlier in the medical images based on the hierarchical clustering representation. In some embodiments, the cluster manager 134 can generate clusters based on a K-means technique. The shared global characteristic can include a shading or mean intensity of an image that corresponds to an unknown view for a mammogram, a foreign object in breast tissue, and the like. The outlier can indicate that a medical image corresponds to an unknown view or angle of a mammogram, a foreign object identified in breast tissue of a mammogram, and the like. In some examples, the medical image corresponds to mammograms and the at least one outlier corresponds to a magnification or compression view within the medical image. In some embodiments, the cluster manager 134 can remove outlier medical images prior to training of further machine learning models such as classification of mammograms according to likelihood of containing a cancerous lesion.

At block 312, the revised medical image manager 136 can generate an alert indicating that a revised set of medical image data is generated, the revised set of medical image data to exclude the at least one outlier. In some embodiments, generating the revised set of medical image data can include transmitting the revised medical image data to a remote device and modifying a user interface to indicate that outliers have been removed from the medical image data set.

The process flow diagram of FIG. 3 is not intended to indicate that the operations of the method 300 are to be executed in any particular order, or that all of the operations of the method 300 are to be included in every case. Additionally, the method 300 can include additional operations. In some embodiments, the method 300 can include encoding the medical images based on a distance function and a representation of the image patches in an auto-encoder latent space.

Figure 4:
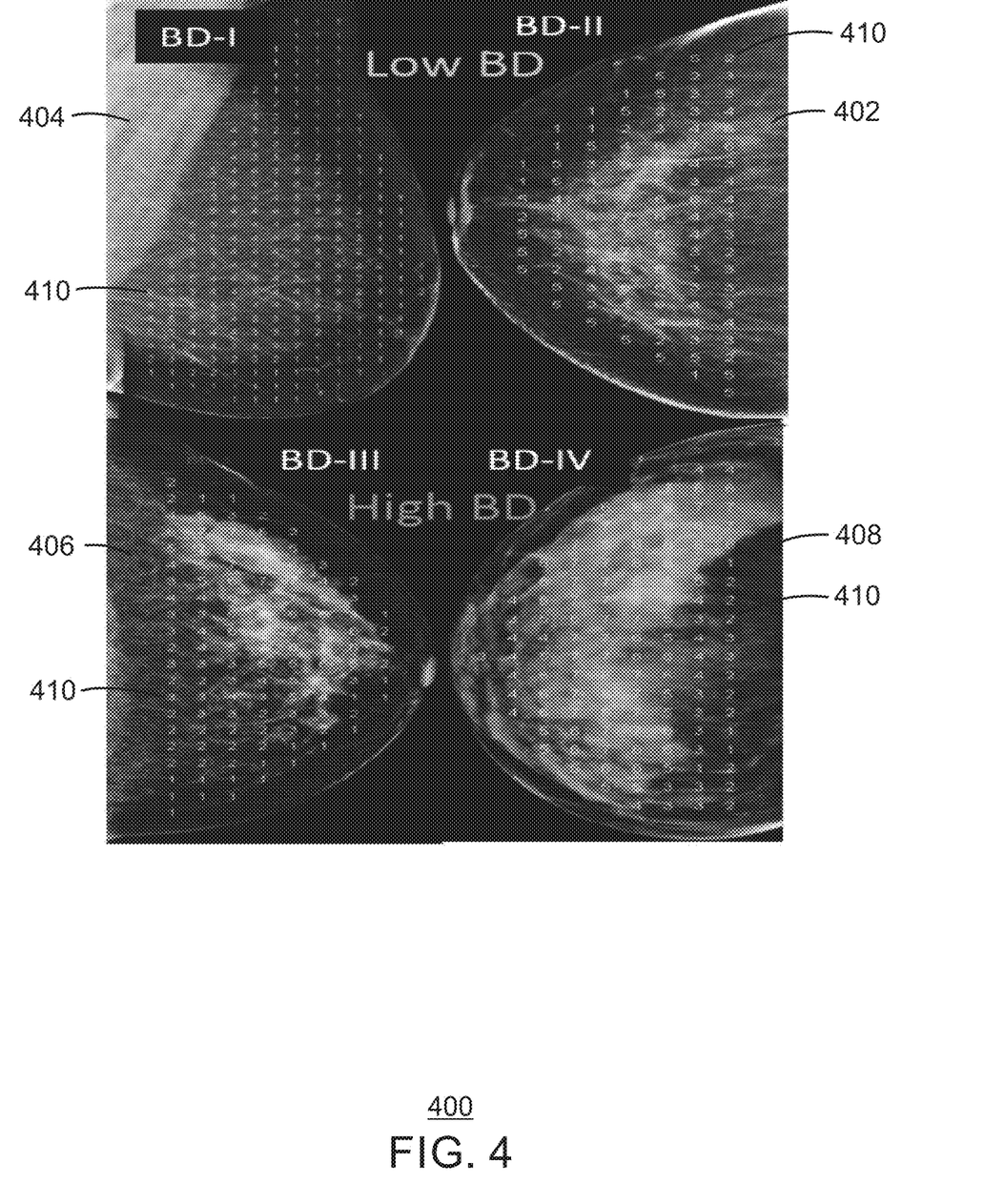
FIG. 4 is a set of example images of mammograms encoded based on tissue type.

FIG. 4 is a set of example images 400 of mammograms encoded based on tissue type. Each image 402, 404, 406, and 408 include numbers 410, which correspond to a mean intensity of a patch region of the images 402, 404, 406, and 408. For example, a one value can indicate a dark shading, while an eight value can indicate a light shading. Values two through seven can indicate shadings that transition from the dark shading to the light shading. In some examples, dark shading corresponds to fat tissue, while light shading corresponds to fibroglandular tissue. An amount of fibroglandular tissue that exceeds a predetermined threshold can indicate a higher risk for medical condition, such as breast cancer. The image 402 illustrates an example with low breast density, image 404 illustrates an example with slightly higher breast density, image 406 includes even higher breast density, and image 408 illustrates an extremely dense breast. In some examples, the set of images 400 can include any suitable number of patches or numbers 402. The set of images 400 can include mammogram images comprising x-ray data of breast tissue, among others.

Figure 5A:
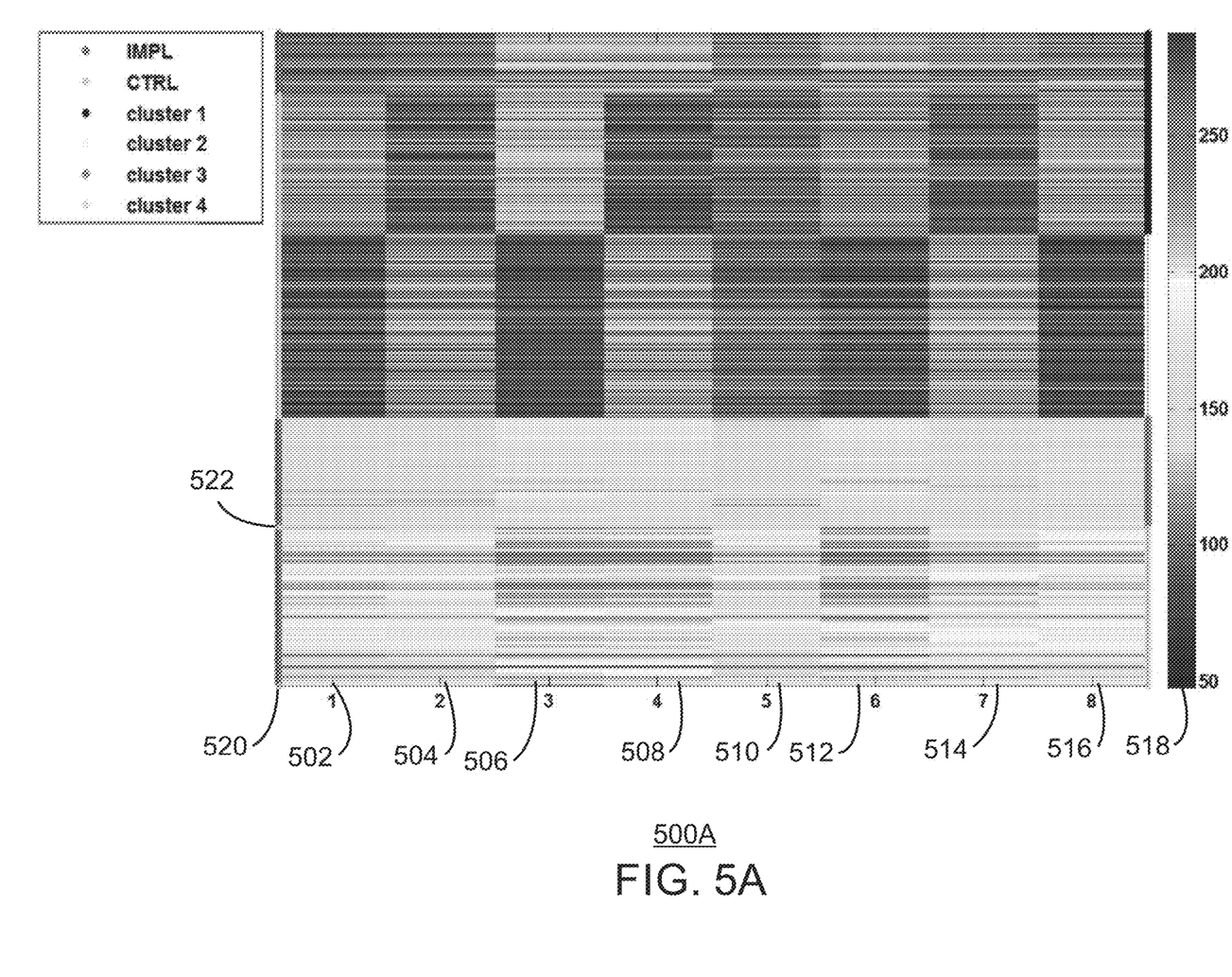
FIGS. 5A-5C depict an example of image signatures based on clustered image distances and a false negative and a false positive image example.
Figure 5B:
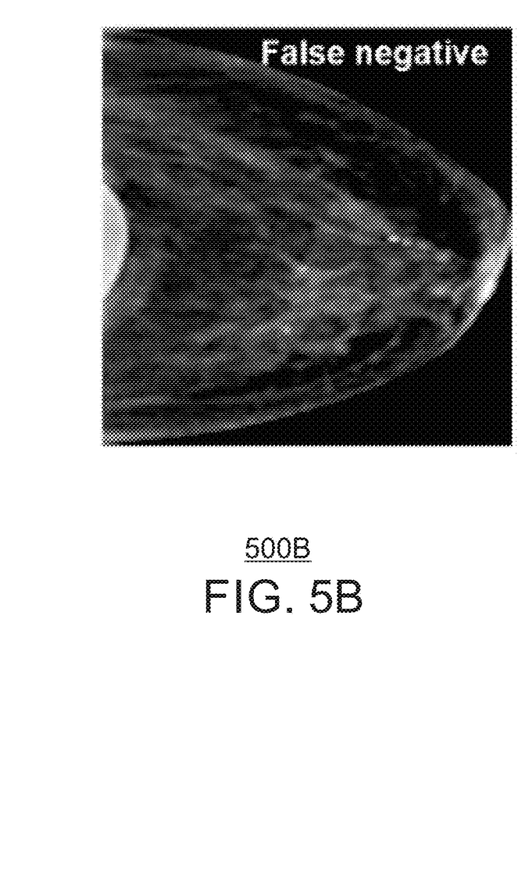
Figure 5C:
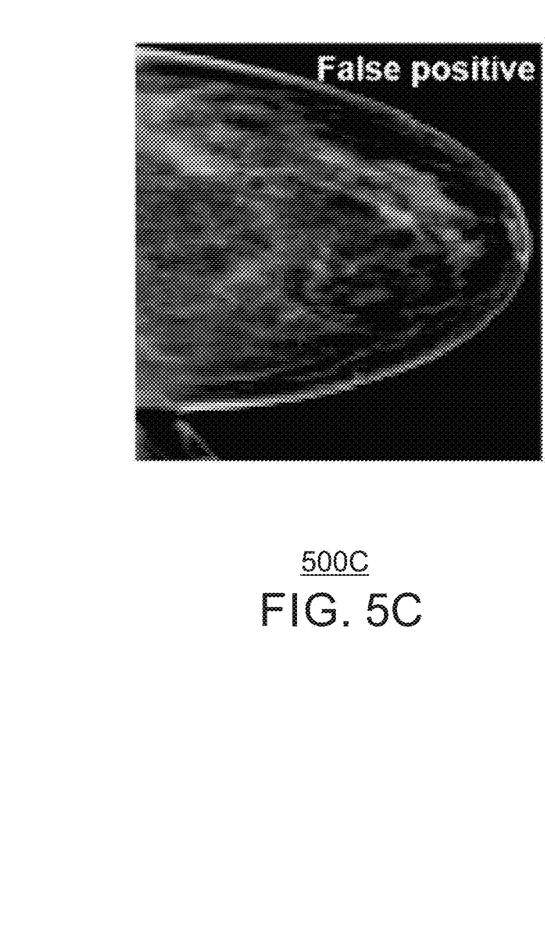

FIG. 5A is an example depiction of re-clustered image distances. Each row in the map 500 presents the distances of an encoded image from each of the cluster centers generated at block 304. There are eight clusters 502, 504, 506, 508, 510, 512, 514, and 516 for this specific example. In some examples, the distance signatures can be re-clustered as illustrated in FIG. 5A. The new clusters are presented and color coded on the right bar 518 and the ground truth on the left bar 520. In this case the implants are associated with clusters 1 and 2 and the control set with clusters 3 and 4. In some examples, a dark color corresponds to an implant image and a light color corresponds to a control image. The image 500B of FIG. 5B illustrates a false positive and the image 500C of FIG. 5C illustrates a false-negative classification, two image samples from the light color section in the bottom 522 of the left bar 520 of FIG. 5A.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
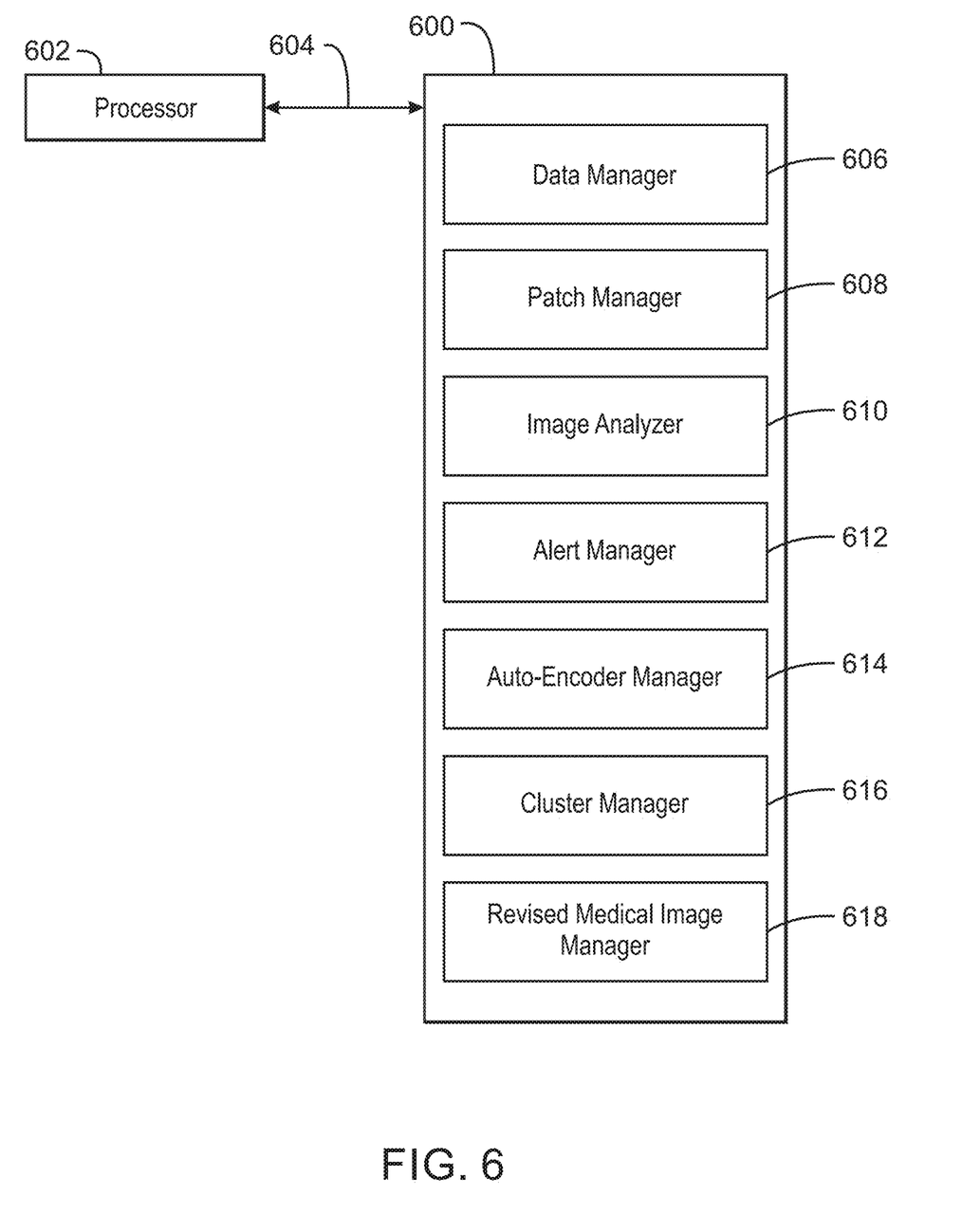
FIG. 6 is a block diagram of an example of a tangible, non-transitory computer-readable medium that can analyze medical images.

Referring now to FIG. 6, a block diagram is depicted of an example of a tangible, non-transitory computer-readable medium that can analyze medical images. The tangible, non-transitory, computer-readable medium 600 may be accessed by a processor 602 over a computer interconnect 604.

Furthermore, the tangible, non-transitory, computer-readable medium 600 may include code to direct the processor 602 to perform the operations of the current method. For example, a data manager 606 can detect a set of medical images and partition each medical image into a plurality of non-overlapping patches. In some examples, a patch manager 608 can generate a sorted set of patch clusters derived from the medical images, wherein the patch clusters are sorted based on a type of tissue identified in each of the medical images. In some embodiments, an image analyzer 610 can generate a digital representation of a percentage of the type of tissue calculated for each of the medical images. In some embodiments, an alert manager 612 can transmit an alert in response to detecting that the percentage of the type of tissue for at least one image exceeds a predetermined threshold.

In some examples, the non-transitory, computer-readable medium 600 can also include an auto-encoder manager 614 that can train an auto-encoder to detect latent space features within a set of medical images. Additionally, the non-transitory, computer-readable medium 600 can include a cluster manager 616 that can generate a set of clusters based on encoding of the medical images with the latent space features. The cluster manager 616 can also generate an encoding of the medical images based on distances between the medical images and the cluster centers. Additionally, the cluster manager 616 can generate a hierarchical clustering representation of the encoded medical images. Furthermore, the cluster manager 616 can detect at least one outlier in the medical images based on the hierarchical clustering representation. Moreover, the non-transitory, computer-readable medium 600 can include a revised medical image manager 618 that can generate an alert indicating that a revised set of medical image data is generated, the revised set of medical image data to exclude the at least one outlier.

It is to be understood that any number of additional software components not shown in FIG. 6 may be included within the tangible, non-transitory, computer-readable medium 600, depending on the specific application. Furthermore, fewer software components than those shown in FIG. 6 can be included in the tangible, non-transitory, computer-readable medium 600.

Figure 7:
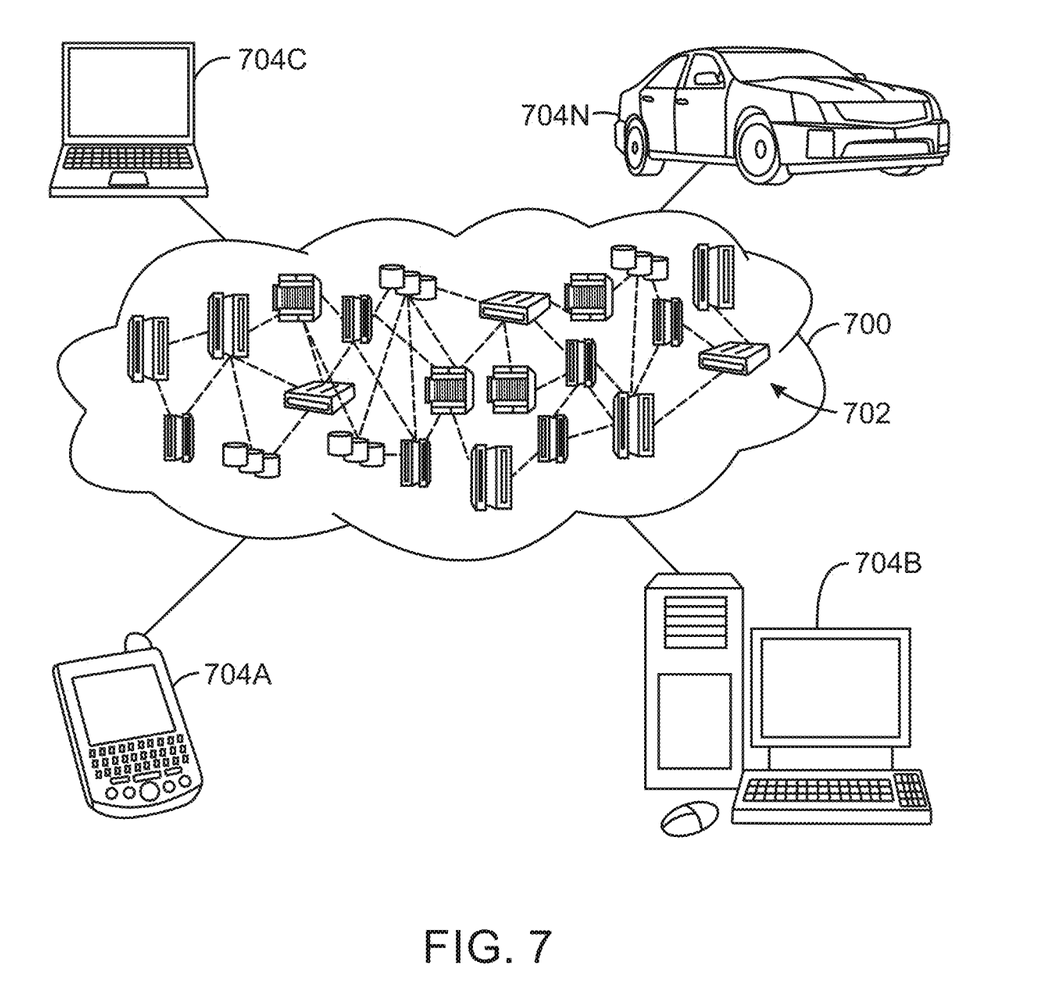
FIG. 7 depicts an illustrative cloud computing environment according to an embodiment described herein.

Referring now to FIG. 7, illustrative cloud computing environment 700 is depicted. As shown, cloud computing environment 700 comprises one or more cloud computing nodes 702 with which local computing devices used by cloud consumers, such as, for example, personal digital assistant (PDA) or cellular telephone 704A, desktop computer 704B, laptop computer 704C, and/or automobile computer system 704N may communicate. Nodes 702 may communicate with one another. They may be grouped (not shown) physically or virtually, in one or more networks, such as Private, Community, Public, or Hybrid clouds as described hereinabove, or a combination thereof. This allows cloud computing environment 700 to offer infrastructure, platforms and/or software as services for which a cloud consumer does not need to maintain resources on a local computing device. It is understood that the types of computing devices 704A-N shown in FIG. 7 are intended to be illustrative only and that computing nodes 702 and cloud computing environment 700 can communicate with any type of computerized device over any type of network and/or network addressable connection (e.g., using a web browser).

Figure 8:
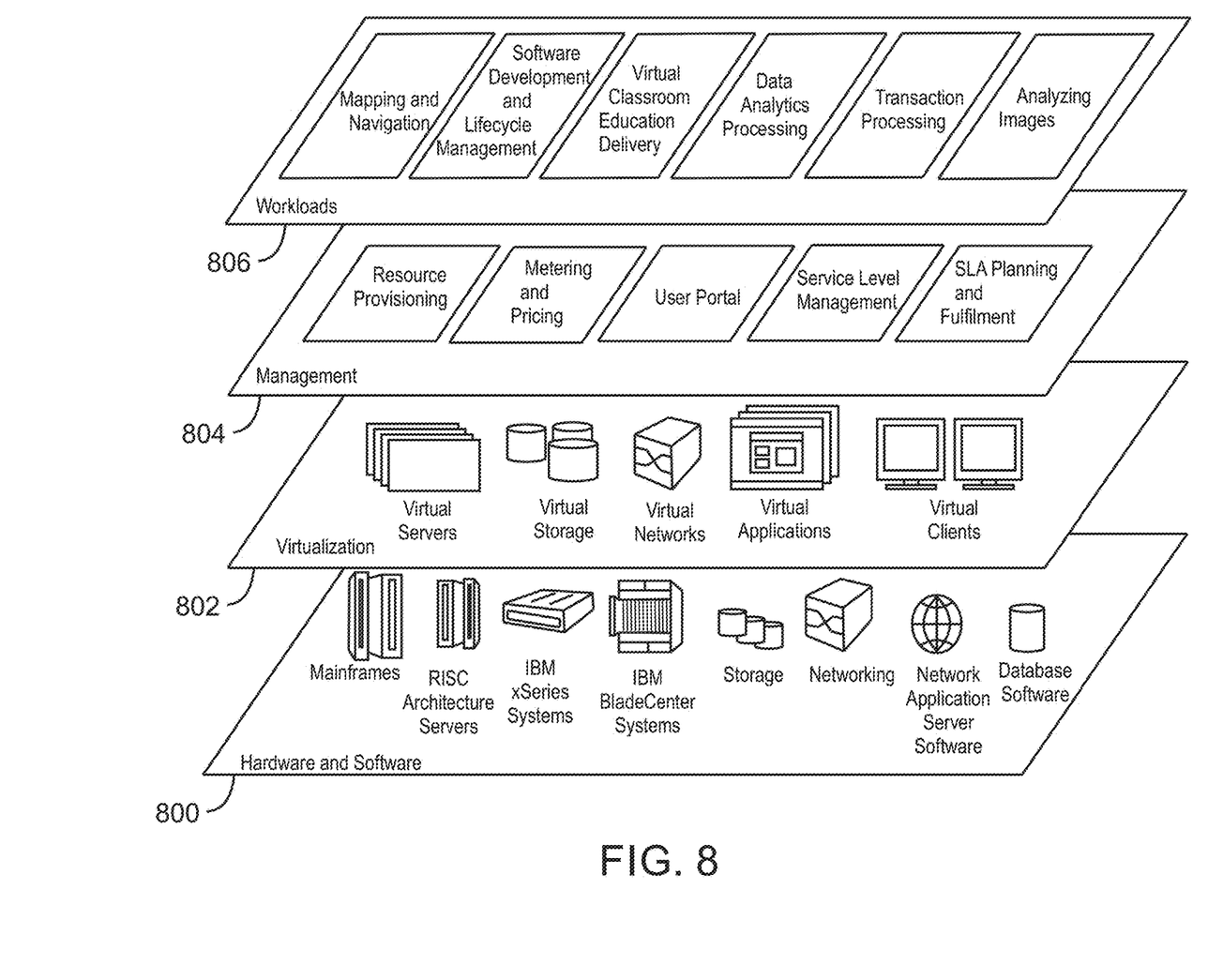
FIG. 8 depicts a set of functional abstraction layers provided by a cloud computing environment according to an embodiment described herein.

Referring now to FIG. 8, a set of functional abstraction layers provided by cloud computing environment 700 (FIG. 7) is shown. It should be understood in advance that the components, layers, and functions shown in FIG. 8 are intended to be illustrative only and embodiments of the invention are not limited thereto. As depicted, the following layers and corresponding functions are provided.

Hardware and software layer 800 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 802 provides an abstraction layer from which the following examples of virtual entities may be provided: virtual servers; virtual storage; virtual networks, including virtual private networks; virtual applications and operating systems; and virtual clients. In one example, management layer 804 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 806 provides examples of functionality for which the cloud computing environment may be utilized. Examples of workloads and functions which may be provided from this layer include: mapping and navigation; software development and lifecycle management; virtual classroom education delivery; data analytics processing; transaction processing; and analyzing medical images.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for analyzing image data, comprising:
a processor to:
  train an auto-encoder to detect latent space features within a set of medical images;
  generate a set of clusters based on encoding of the medical images with the latent space features;
  generate an encoding of the medical images based on distances between the medical images and cluster centers;
  generate a hierarchical clustering representation of the encoded medical images;
  detect at least one outlier in the medical images based on the hierarchical clustering representation;
  exclude the at least one outlier from the set of medical images, generating a revised set of medical images;
  partition each medical image within the revised set of medical images into a plurality of patches;
  generate a sorted set of patch clusters derived from the patches of the revised set of medical images, wherein the patch clusters are sorted based on an average brightness of each patch cluster;
  generate a digital representation of one of the medical images within the revised set of medical images based on a prevalence of the patches from different clusters, wherein the prevalence of the patches indicate different types of tissues and a percentage of the types of tissues calculated for each of the medical images; and
  transmit an alert in response to detecting that the percentage of the type of tissue for at least one image exceeds a predetermined threshold.

2. The system of claim 1, wherein the medical images correspond to mammograms, and wherein the percentage of the type of tissue corresponds to a breast density.

3. The system of claim 1, wherein the processor is to calculate the type of tissue for each patch cluster within the revised set of medical images based on an unsupervised machine learning technique.

4. The system of claim 1, wherein the processor is to divide each medical image into a predetermined number of overlapping bounding boxes that correspond to the patch clusters.

5. The system of claim 2, wherein the processor is to calculate the breast density based on a prevalence of tissue dense patch clusters in a mammogram, the tissue dense patch clusters being a subset of the patch clusters.

6. The system of claim 5, wherein the processor is to detect a likelihood of a medical condition in response to detection of a prevalence of patches from the tissue dense patch clusters.

7. The system of claim 1, wherein the medical images correspond to mammograms, and wherein the at least one outlier corresponds to at least one of a foreign object residing within one or more medical images or a non-standard imaging view within one or more medical images.

8. The system of claim 1, wherein the medical images correspond to mammograms, and wherein the processor is to conduct a K-means clustering on generated patch representations to use cluster frequencies in each mammogram as a breast density indicator.

9. The system of claim 1, wherein the processor is to encode the medical images based on a distance function and a representation of the medical images by distances from the cluster centers.

10. A system for analyzing medical images comprising:
a processor to:
  train an auto-encoder to detect latent space features within a set of medical images;
  generate a set of clusters based on encoding of the medical images with the latent space features;
  generate an encoding of the medical images based on distances between the medical images and cluster centers;
  generate a hierarchical clustering representation of the encoded medical images;
  detect at least one outlier in the medical images based on the hierarchical clustering representation;
  exclude the at least one outlier from the set of medical images, generating a revised set of medical images; and
  generate an alert indicating that the revised set of medical images has been generated, the revised set of medical images to be used for a machine learning based training set.

11. The system of claim 10, wherein the medical images correspond to mammograms and the at least one outlier corresponds to a foreign object residing within the medical images.

12. The system of claim 10, wherein the medical images correspond to mammograms and the at least one outlier corresponds to a magnification or compression view within the medical images.

13. A non-transitory computer readable storage medium, comprising program instructions that are executable by a processor to cause the processor to:
  train an auto-encoder to detect latent space features within a set of medical images;
  generate a set of clusters based on encoding of the medical images with the latent space features;
  generate an encoding of the medical images based on distances between the medical images and cluster centers;
  generate a hierarchical clustering representation of the encoded medical images;
  detect at least one outlier in the medical images based on the hierarchical clustering representation;
  exclude the at least one outlier from the set of medical images, generating a revised set of medical images;
  partition each medical image within the revised set of medical images into a plurality of overlapping or non-overlapping patches;
  generate a sorted set of patch clusters derived from the patches of the revised set of medical images, wherein the patch clusters are sorted based on an average brightness of each patch cluster;

generate a digital representation of one of the medical images within the revised set of medical images according to a prevalence of the patches from different clusters, wherein the prevalence of the patches indicate different types of tissues and a percentage of the types of tissues calculated for each of the medical images; and transmit an alert in response to detecting that the percentage of the type of tissue for at least one image exceeds a predetermined threshold.

14. The non-transitory computer readable storage medium of claim 13, wherein the medical images correspond to mammograms, and wherein the percentage of the type of tissue corresponds to a breast density.

15. The non-transitory computer readable storage medium of claim 13, wherein the program instructions are executable by the processor to cause the processor to calculate the type of tissue for each patch cluster within the revised set of medical images based on an unsupervised machine learning technique.

16. The non-transitory computer readable storage medium of claim 13, wherein the program instructions are executable by the processor to cause the processor to divide each medical image into a predetermined number of overlapping bounding boxes that correspond to the patch clusters.

17. The non-transitory computer readable storage medium of claim 14, wherein the program instructions are executable by the processor to cause the processor to calculate the breast density based on a prevalence of tissue dense patch clusters.

18. The non-transitory computer readable storage medium of claim 17, wherein the program instructions are executable by the processor to cause the processor to detect a likelihood of a medical condition in response to a detected mean intensity of a patch cluster being above a threshold.

19. The non-transitory computer readable storage medium of claim 13, wherein the medical images correspond to mammograms and the at least one outlier corresponds to at least one of a foreign object residing within one or more medical images or a non-standard imaging view within one or more medical images.

20. The non-transitory computer readable storage medium of claim 19, wherein the non-standard imaging view is a magnification view or a compression view.

* * * * *